(12) United States Patent
Kahn et al.

(10) Patent No.: US 10,166,089 B2
(45) Date of Patent: Jan. 1, 2019

(54) MAXILLARY PROTRACTION DEVICE

(71) Applicant: Sandra Vivian Kahn, Lao pobla de Vallbona (ES)

(72) Inventors: Sandra Vivian Kahn, La pobla de Vallbona (ES); Mabel Flores Cerceda, Silla (ES); Ilan Kahn Leventhal, La pobla de Vallbona (ES)

(73) Assignee: Sandra Vivian Kahn, La pobla de Vallbona (ES)

( * ) Notice: Subject to any disclaimer, the term of this patent is extended or adjusted under 35 U.S.C. 154(b) by 0 days.

(21) Appl. No.: 15/430,540

(22) Filed: Feb. 13, 2017

(65) Prior Publication Data
US 2018/0028282 A1    Feb. 1, 2018

(30) Foreign Application Priority Data

Jul. 28, 2016 (ES) .................... 201631041

(51) Int. Cl.
A61C 7/06 (2006.01)
A61B 5/00 (2006.01)
A61B 5/01 (2006.01)

(52) U.S. Cl.
CPC .............. *A61C 7/06* (2013.01); *A61B 5/0008* (2013.01); *A61B 5/01* (2013.01); *A61B 2560/0475* (2013.01)

(58) Field of Classification Search
CPC .................................. A61C 7/06; A61C 7/065
See application file for complete search history.

(56) References Cited

U.S. PATENT DOCUMENTS

| | | | | |
|---|---|---|---|---|
| 1,976,639 A * | 10/1934 | Spitler | ..................... | A61C 7/00 33/513 |
| 2,151,458 A * | 3/1939 | Allen | | |
| 3,885,310 A * | 5/1975 | Northcutt | ................. | A61C 7/06 433/5 |
| 5,890,891 A * | 4/1999 | Doyle | ...................... | A61C 7/06 433/5 |
| 6,213,765 B1 * | 4/2001 | Standerwick | ............ | A61C 7/06 433/5 |
| 7,011,642 B2 * | 3/2006 | Greene et al. | | |

FOREIGN PATENT DOCUMENTS

WO     WO 2016/012970      *   1/2016

\* cited by examiner

*Primary Examiner* — Ralph Lewis

(57) ABSTRACT

Maxillary protraction device comprising a cranial support (1) that may be attached with straps (4) or similar on the forehead of the user. A guide (8) in a central position on the support (1) attaches to the upper end (9) of a vertical rod (2), at the lower end (13) of which a horizontal rod (3) is arranged with gripping points for the rubber bands that provide a tractive force on the jaw to be treated. Between the two ends (9, 13) of the rod, a ratchet mechanism (12) or similar may be arranged to adjust the angle, while the lower end (13) can be telescopic.

10 Claims, 6 Drawing Sheets

MAXILLARY PROTRACTION DEVICE

RELATED APPLICATION

This application claims the benefit of priority of Spanish Patent Application No. 201631041 filed Jul. 28, 2016, the contents of which are incorporated herein by reference in their entirety.

FIELD AND BACKGROUND OF THE INVENTION

The present invention relates to a maxillary protraction device, for the treatment of malocclusion, preferably for class III malocclusion (upper jaw).

It is applicable in the field of health, and more specifically in orthodontics.

Many devices are used to treat malocclusion, which due to their complexity and poor ergonomics, as well as their 'peculiar' aesthetic appearance, are to be used by the user only at home, or rather when the user is resting/sleeping. Some examples can be seen in ES2280617T3, U.S. Pat. No. 4,706,301A or US20100190126.

This type of device significantly impairs one's ability to fall asleep, since it is made up of different support points on different parts of the face, head and even the neck or torso of the patient. All of this without forgetting that it has rubber bands and interacts with the fixed orthodontic appliances that the patient has on his teeth, and the horizontal rod of the device. These rubber bands essentially prevent any movement of the mouth and they maintain the mouth completely closed, only allowing for nasal breathing.

That is why the technology of this type of device, if it truly does complement and provide significant progress in the treatment of malocclusion, speeding up in a very relevant way the alignment process of the jaw (upper or lower), is continuously advancing, always in the interest of creating the most ergonomic device possible, while at the same time being less invasive on the patient.

With the aforementioned objective, the applicant has devised the device of the invention, which provides a significantly improved support for the existing elements of maxillary protraction.

SUMMARY OF THE INVENTION

The invention consists of a maxillary protraction device according to the claims.

This device offers two main novelties, the first related to ergonomics and the second to versatility:
  The ergonomics of the support of the rods that form part of it, like a helmet that is placed on the front of the skull,
  And the many possibilities of adjusting the position of the vertical rod, which is fixed to the horizontal rod that acts as a support and receiver of rubber bands, which are mounted on at least two points of the orthodontic appliance of the patient and connect the interior device to the rod of the device of the invention.

This versatility as it relates to adjustment ensures ergonomics and correct attachment; in addition, it is hardly intrusive, which means it can be used at any time of the day.

Specifically, the maxillary protraction device has a cranial support that can be adjusted with straps or another similar method (for example, by using elastic material to form part of a helmet or hat) on the forehead of the user. The support comprises a guide in a central position, upon which the upper end of a vertical rod is fixed. The lower end of the vertical rod has a horizontal rod with gripping points for the rubber bands that provide a tractive force on the jaw to be treated.

A number of changes or preferred embodiments can be made to this basic embodiment, of which the following stand out:
  The vertical rod also comprises a central part that is attached to the upper end by a ratchet mechanism or similar which allows the angle to be adjusted with enough resistance to withstand the angular momentum generated by the rubber bands.
  The lower end is telescopic.
  The support comprises cheek pieces for the attachment of straps or similar.
  The guide may consist of two parallel plates, preferably with a base that has the same curvature as the upper end of the vertical rod (which does not have to be straight).

Another embodiment of the device object of the present invention allows for the improvement of the maneuverability of the user, especially when they are lying down, since it allows for practically all the movements of the patient's neck and head as they are sleeping, in other words, it makes it possible to move the head and neck with practically the same freedom as they would have without wearing the device of the invention.

For this reason, the vertical rod articulates on the guide by means of an articulating element. Additionally, said vertical rod has an interior rod that has at its end a spherical articulation similar to a ball joint, mounted on a rotating support and wherein said spherical articulation and the rotating support are mounted on a fixed thorax support plate.

Said fixed plate incorporates a plurality of through holes to hold the optional fastening straps, which contribute to keeping the fixed plate as well as the rest of the device in the working position established by the doctor.

On the other hand, and in order to allow for the lateral movements of the patient's head, without diminishing the effectiveness of the device, the horizontal rod is mounted on a supporting piece that is located on top of a casing fixed and secured to the vertical rod, meaning that the supporting piece rotates horizontally over the vertical rod in both directions, maintaining the tension exerted by the rubber bands positioned on the horizontal rod constant.

BRIEF DESCRIPTION OF THE SEVERAL VIEWS OF THE DRAWINGS

In order to make the invention more readily understandable, the following figures are included.

DESCRIPTION OF SPECIFIC EMBODIMENTS OF THE INVENTION

Next, several embodiments of the invention will be described briefly, by way of illustrative, non-limitative examples thereof.

Figure 1:
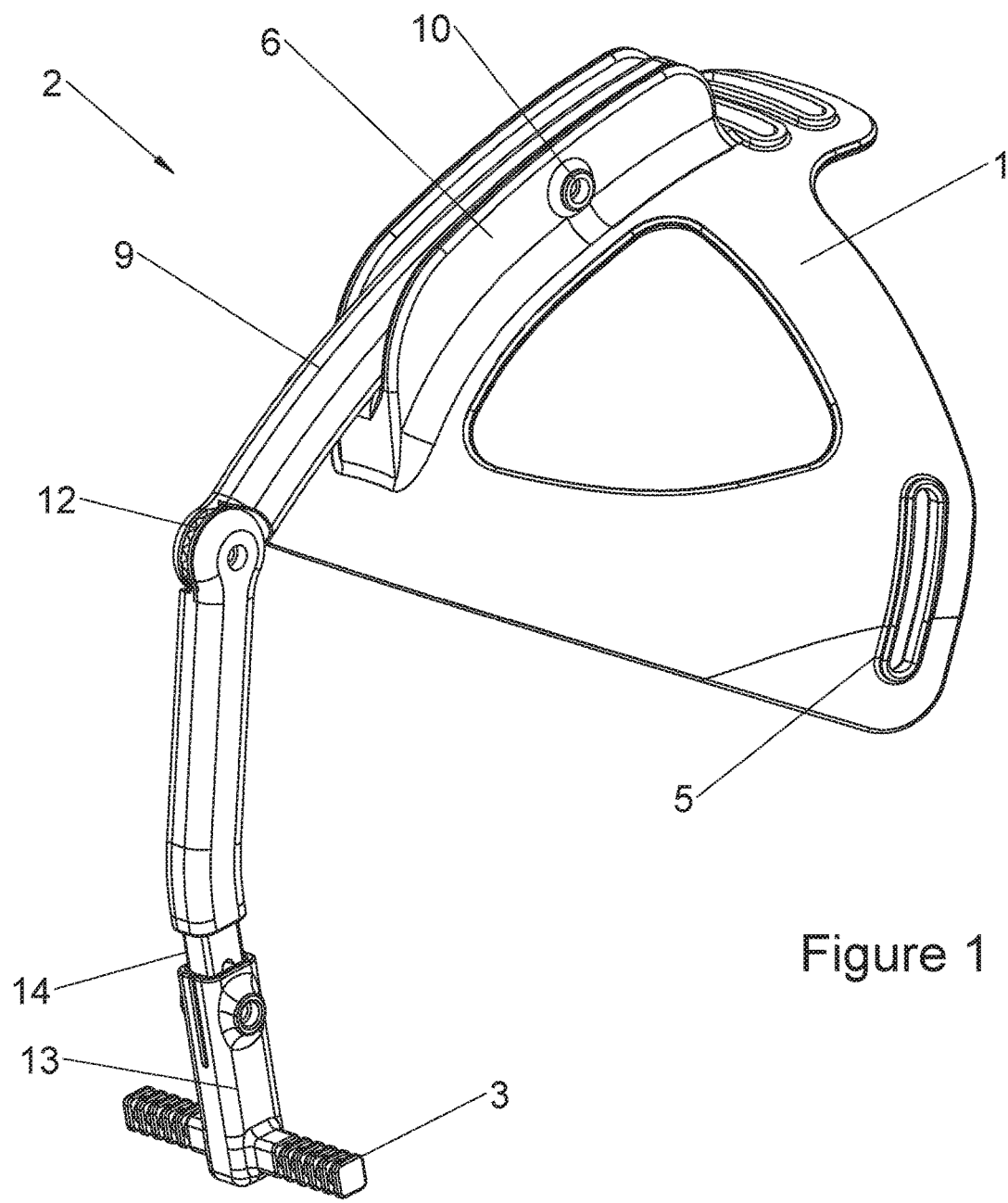
FIG. 1: A first exemplary embodiment of a cranial support, and the rods.

The invention, as shown in FIG. 1, comprises a cranial support (1), a vertical rod (2) and a horizontal rod (3). The support (1) will be placed approximately on the frontal bone of the cranium and attached by straps (4) or another similar method. For this reason, it has a series of holes (5) for the placement of the fixing straps (4) and it's positioning on the head of the user, all of which are adjustable through conventional means, such as Velcro, among others.

The cranial support (1) of the represented embodiments comprises two parallel plates (6) that protrude from it, in a position that will correspond to the center of the user's forehead. There is a base (7) between these two plates (6) which comprises the bottom of a guide (8) through with the upper end (9) of the vertical rod (2) moves. The curvature of the base (7) will correspond to that of the upper end (9) of the vertical rod (2), so that it can be placed and be perfectly coupled to any point on the guide (8).

The guide (8) can have other forms, for example, it can be a tube to which the vertical rod (2) is attached.

Figure 2:
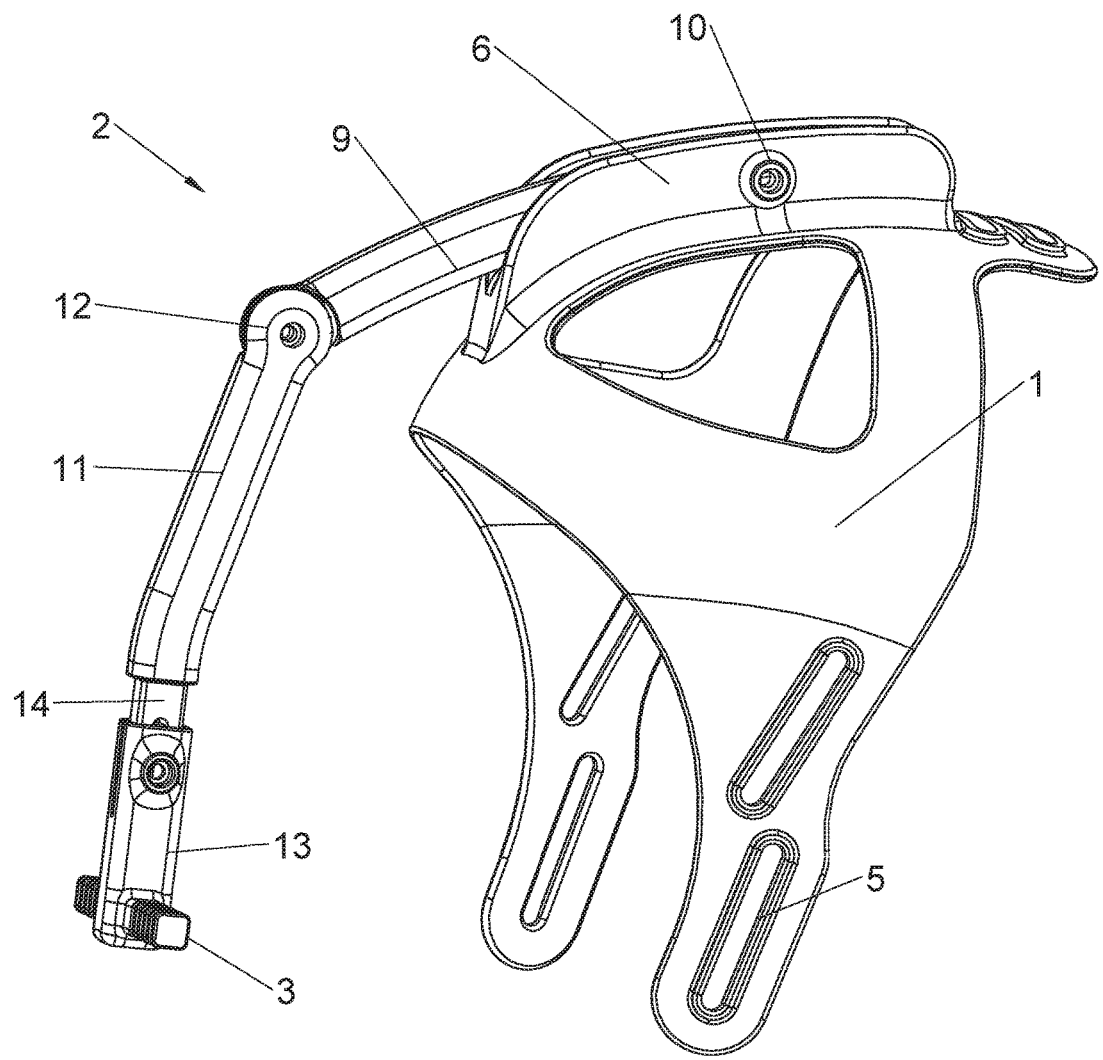
FIG. 2: A second exemplary embodiment of a different version of the cranial support.

Three ways of making the support (1) have been shown in the figures. The most relevant is FIG. 2, where the cranial support (1) is extended in front of the ears so that the holes (5) are farther away from each other. This type will be preferably used for children.

The cranial support (1) can be formed using a mold taken of the patient. Likewise, it can be made with a transparent material, such as methacrylate, in order to minimize visual impact. If preferred, it can have another type of finishing, especially when it will be used by children. It is also possible to place inner padding on the device to make it more comfortable.

The vertical rod (2) is preferably divided into three parts:
- Upper end (9): the part that is mounted on the cranial support (1) and with a relative position that can be adjusted on the guide (8) through one or more locking points (10), which will allow it to move up or down through the channel of the cranial support (1).
- Central part (11): it will be attached to the upper end (9) of the vertical rod (2) and its relative position to this part can be adjusted by a ratchet mechanism (12) or similar, which will allow the approximation or separation of the lower end (13) to the patient.
- Lower end (13): it integrally incorporates the horizontal rod (3) on its free end and its length can be adjusted by means of a telescopic element (14).

The ends (9, 13) or the central part (11) can be straight, curved or bent if considered convenient structurally or aesthetically.

In its most common embodiment, the horizontal rod (3) is made up of two straight halves, one on each side of the free end of the vertical rod (2). The horizontal rod (3) can be formed in various ways, for example, with a more aesthetic curvature. In any case, the horizontal rod (3) will have gripping points for the rubber bands that provide a tractive force on the jaw to be treated.

There are other embodiment alternatives for the vertical rod (2), for example, with removable elements of different sizes, so that medical staff can choose the proper length for each case without needing to adjust angles. However, the version described is considered to be the most advantageous.

Figure 3:
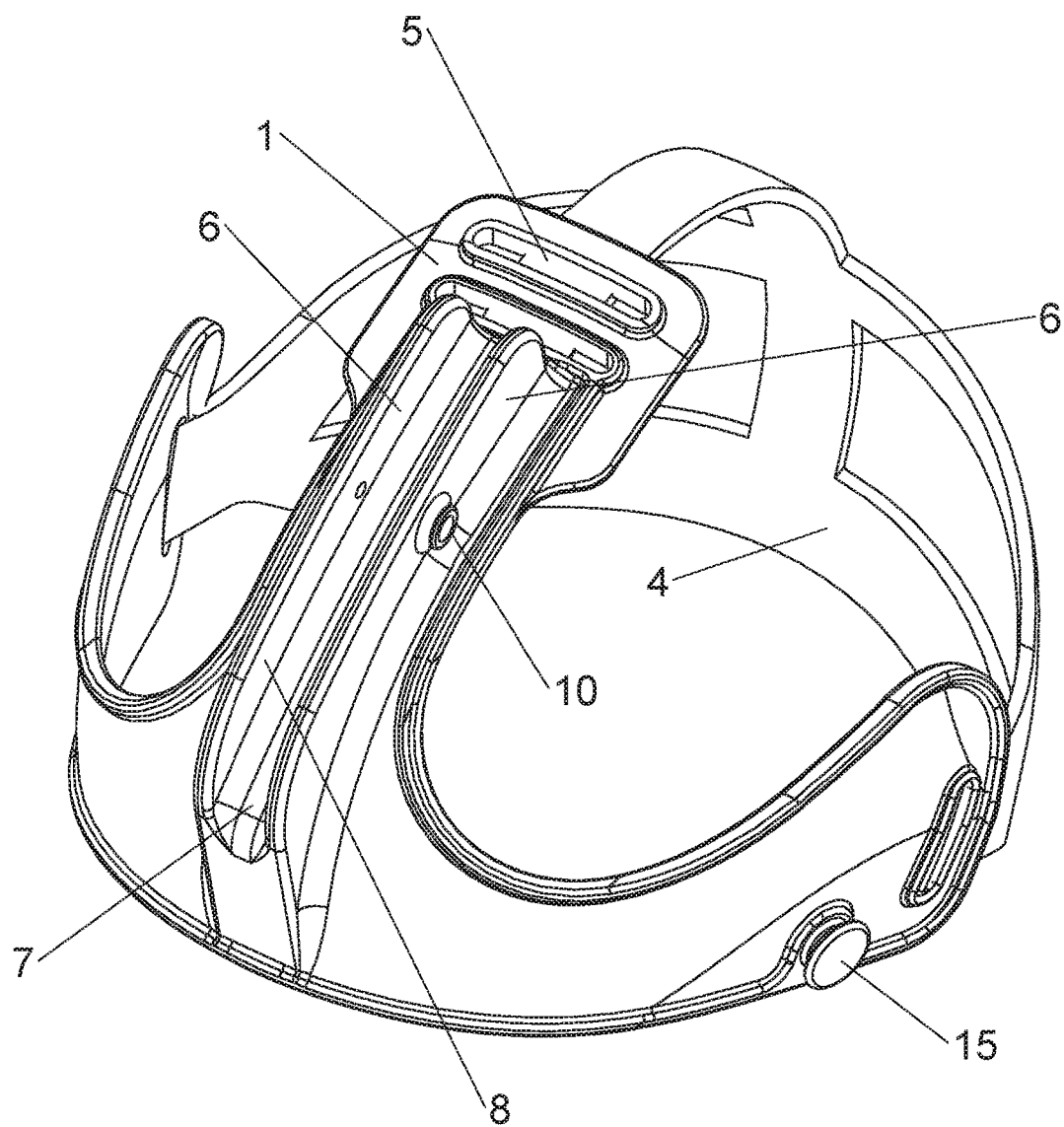
FIG. 3: A third exemplary embodiment of the cranial support, with attachment straps.

The device can be completed with a pair of symmetrical attachments (15) that are approximately located on the temples, each generally formed by elements of a circular section (see FIG. 3). The purpose of these attachments (15) is to hold and support orthodontic headgear, preferably of metal, which can be used in cases where it is necessary to intervene on the upper part of the dental arch.

It is important to highlight the many adjustment and guidance points of the preferred vertical rod (2) and, as a result, of the horizontal rod (3). Firstly, this versatility allows it to be adapted to many head and skull sizes of patients, from babies to adults. Secondly, it allows the positioning distance of the horizontal rod (3) to be adjusted, which supports the traction that the rubber bands provide on the orthodontic appliance of the patient and, consequently, on the jaw and/or teeth. The positioning of said horizontal rod (3) is directly proportional to the tractive force of the device of the invention on the jaw to be treated.

Figure 4:
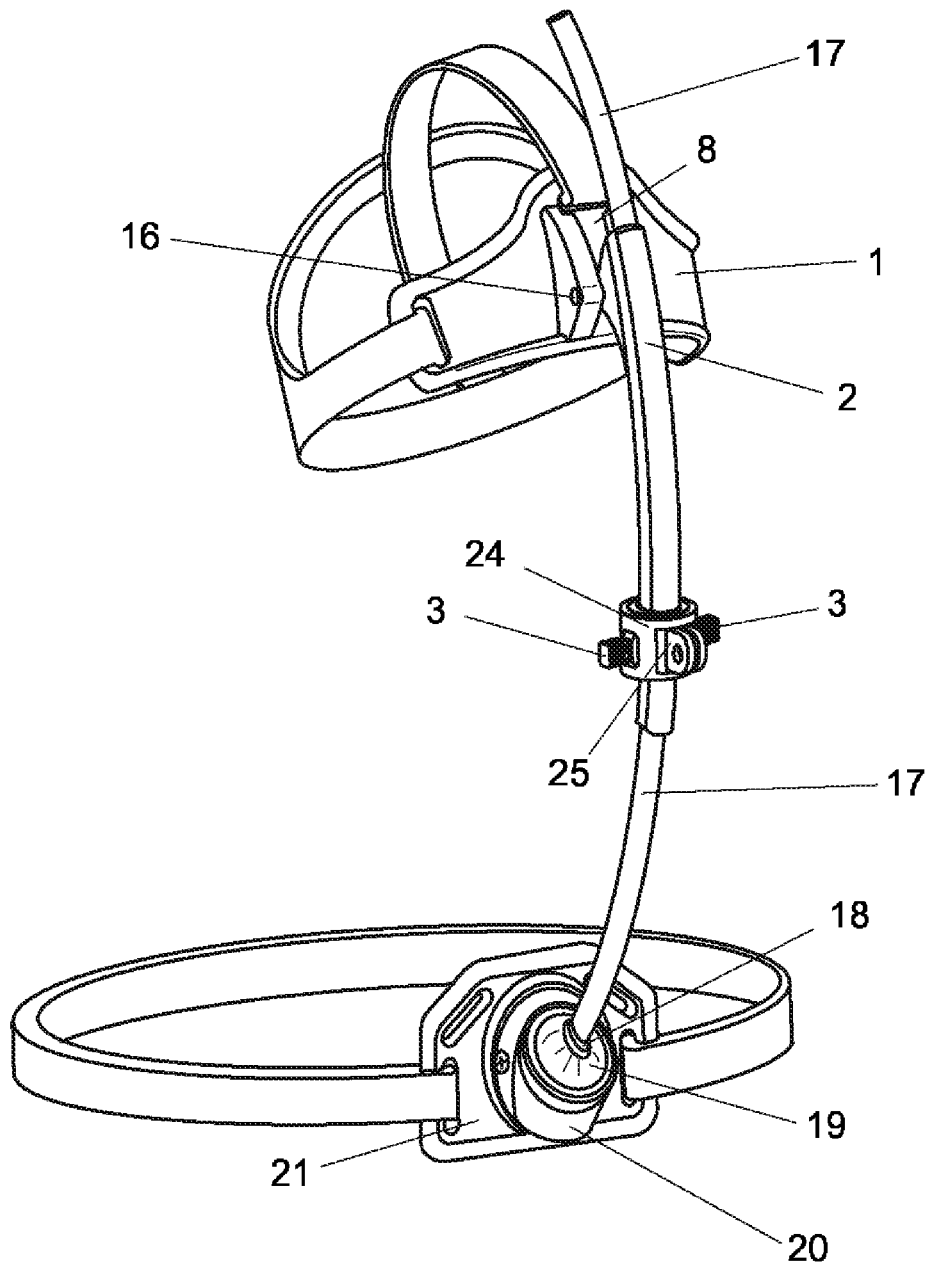
FIG. 4: A fourth exemplary embodiment wherein a fastening device to the patient's thorax is also included.

In another particular embodiment of the invention, the vertical rod (2) articulates on the guide by means of an articulating element (16), as shown in FIG. 4.

In said FIG. 4, the device of the present invention is shown, which also has a fastening device to the patient's thorax, which is made up in the following way. The vertical rod (2) has an interior rod (17) that has at its end (18) a spherical articulation (19) similar to a ball joint, mounted on a rotating support (20) and wherein said spherical articulation (19) and the rotating support (20) are mounted on a fixed thorax support plate (21).

Figure 5:
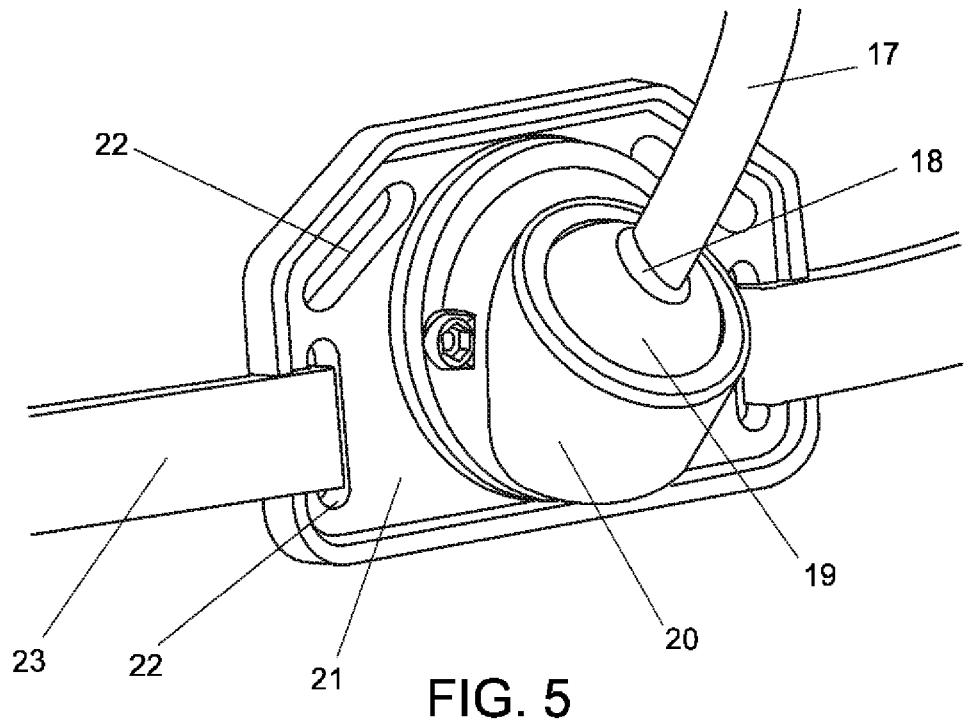
FIG. 5: It shows a front perspective view of the fixed thorax support plate, according to an embodiment of the present invention.
Figure 6:
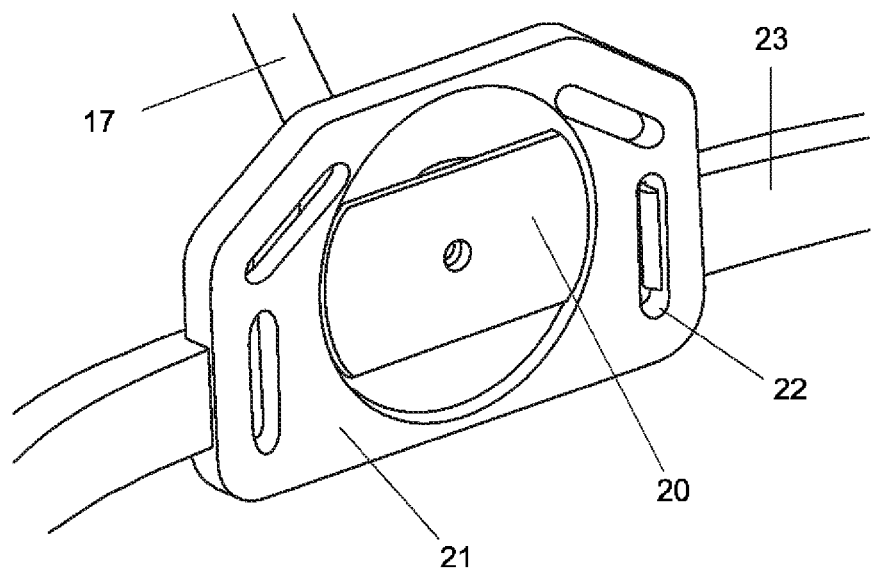
FIG. 6: It shows a rear perspective view of the fixed thorax support plate, according to an embodiment of the present invention.

The fixed plate (21) incorporates a plurality of through holes (22) to hold the optional fastening straps (23), which contribute to keeping the fixed plate (21) as well as the rest of the device in the working position established by the doctor. See FIGS. 5 and 6.

Figure 7:
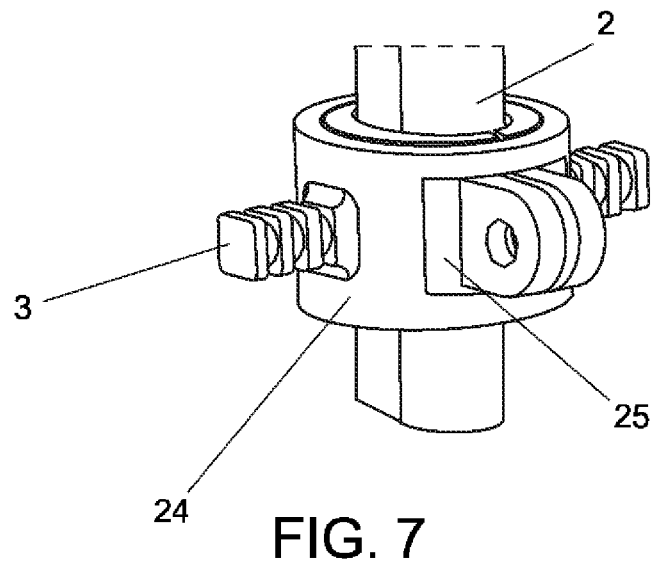
FIG. 7: It shows an exemplary embodiment of the horizontal rod.

Also in FIG. 4, and with more detail in FIG. 7, the horizontal rod (3) is shown mounted on a supporting piece (24) that is located on top of a casing (25) fixed and secured to the vertical rod (2), meaning that the supporting piece (24) rotates horizontally over the vertical rod (2) in both directions, maintaining the tension exerted by the rubber bands in the horizontal rod (3) constant.

Figure 8:
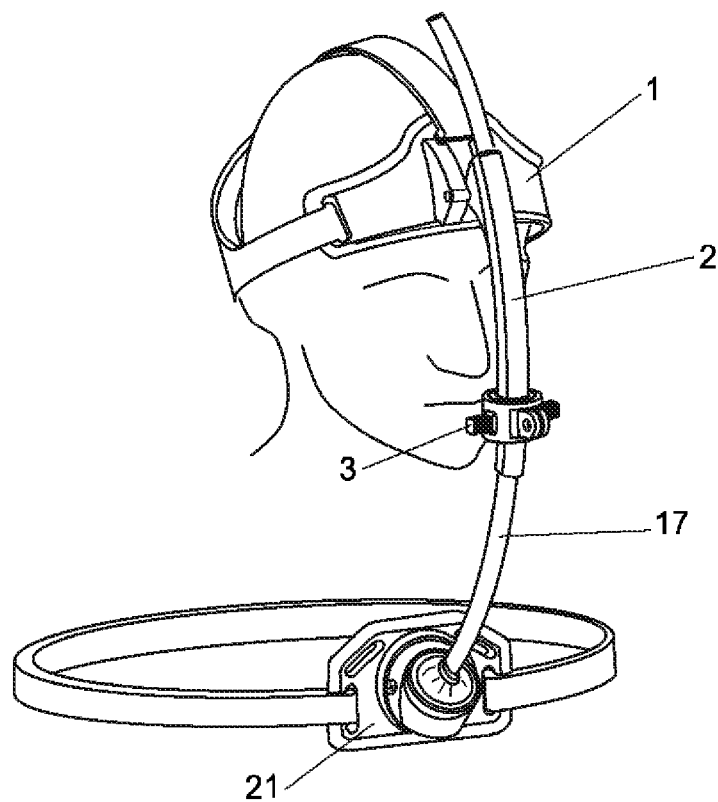
FIG. 8: It represents a particular embodiment of the device of the invention in a form of use, wherein the fastening device to the patient's thorax is also shown.

FIG. 8 shows the previously described particular embodiment of the device object of the present invention, in a form of use; in said FIG. 8 it is possible to see that the interior rod (17) can move inside of the vertical rod (2) in such a way that the fixed plate (21) and its associated elements can be adequately placed on the patient's thorax.

It is recommended to add a sensor that measures the user's body temperature (not shown), which can record and/or transmit the wearing time parameters of the aforementioned device through wireless means or otherwise to a central database. In other words, once the user puts on the device, this element will read theirs body temperature (which is a range value generally between 35 and 39° C.), which implies that the device of the invention has been put on and is working. The exact position may change, but it will be preferably placed at the center of the forehead, taking advantage of the base (7) of the guide (8), and coming in contact with the user's skin.

This additional element allows the specialist to track the patient's use of the device of the invention and be able to monitor the patient's progress, taking into account the effective times of treatment.

What is claimed is:

1. A maxillary protraction device, comprising:
a cranial support configured to be attached over the frontal bone of the cranium of a user;
a guide attached on a central position of the cranial support;
a vertical rod attached to said guide, wherein said vertical rod comprises an upper end configured to be attached to the guide, a central part and a lower end, wherein the central part of the vertical rod is connected to the upper end by a ratchet mechanism configured to adjust the distance of the vertical rod regarding to the user; and,
a horizontal rod attached to the lower end of the vertical rod, wherein the horizontal rod comprises gripping points configured to fix rubber bands between said horizontal rod and an orthodontic appliance of the user, being said rubber bands configured to provide a tractive force on the jaw of the user.

2. The maxillary protraction device according to claim 1, wherein the central part of the vertical rod is connected to the lower end by a telescopic joint configured to adjust the height of the horizontal rod.

3. The maxillary protraction device according to claim 1, wherein the cranial support comprises a series of holes configured to place at least a fixing strap configured to adjust and attach the cranial support to the user's forehead.

4. The maxillary protraction device according to claim 1, wherein the guide comprises two parallel plates protruding from a base fixed to the cranial support and said base being configured to fit the upper end of the vertical rod.

5. The maxillary protraction device according to claim 1, wherein the cranial support comprises a pair of attachments symmetrically located at and above of the user's temples, configured to hold and support an orthodontic extraoral anchorage.

6. The maxillary protraction device according to claim 1, wherein the upper end of the vertical rod is articulately attached to the guide through an articulating element, the vertical rod further comprising an interior rod.

7. The maxillary protraction device according to claim 6, further comprising:
a rotating support mounted on a fixed thorax support plate; and,
a spherical articulation fitted in the rotating support;
wherein said spherical articulation is located at a lower end of the interior rod.

8. The maxillary protraction device according to claim 6, wherein the fixed thorax support plate comprising a plurality of through holes configured to hold a fastening straps.

9. The maxillary protraction device according to claim 6, further comprising:
a supporting piece where the horizontal rod is mounted; and,
a casing fixed and secured to the vertical rod and configured to hold the supporting piece;
wherein the supporting piece is configured to rotate regarding to the vertical rod.

10. The maxillary protraction device according to claim 1, further comprising:
a sensor configured to measure the body temperature of the user and to measure a wearing time of user wears the maxillary protraction device; and,
recording and transmitting means configured to record and/or transmit the wearing time to a central database.

* * * * *